US006806378B2

(12) United States Patent
Tucker et al.

(10) Patent No.: US 6,806,378 B2
(45) Date of Patent: Oct. 19, 2004

(54) PROCESS FOR PREPARING NONRACEMIC CHIRAL ALCOHOLS

(75) Inventors: Charles E. Tucker, Superior, CO (US); Qiongzhong Jiang, Sunnyvale, CA (US)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 10/153,421

(22) Filed: May 21, 2002

(65) Prior Publication Data

US 2003/0171213 A1 Sep. 11, 2003

Related U.S. Application Data

(63) Continuation-in-part of application No. 10/057,826, filed on Jan. 24, 2002.

(51) Int. Cl.[7] .......................... C07F 15/00; C07F 17/02; B01J 31/00
(52) U.S. Cl. ......................... 556/137; 556/21; 502/155; 540/450; 546/217; 548/111; 568/8; 568/17
(58) Field of Search ........................... 502/155; 556/21, 556/137; 540/450; 546/217; 548/111; 568/8, 17

(56) References Cited

U.S. PATENT DOCUMENTS

| | | | |
|---|---|---|---|
| 4,321,414 A | 3/1982 | Costa | |
| 5,716,961 A | 2/1998 | Sands | |
| 5,763,688 A | 6/1998 | Ikariya et al. | |
| 6,037,500 A | 3/2000 | Zhang | |
| 6,258,827 B1 | 7/2001 | Chenard et al. | |
| 6,372,931 B1 | 4/2002 | Blacker et al. | |
| 6,380,416 B2 | 4/2002 | Zhang | |
| 6,399,787 B1 * | 6/2002 | Zhang | 548/469 |
| 6,486,337 B2 | 11/2002 | Burk et al. | |
| 2001/0007872 A1 | 7/2001 | Menniti et al. | |
| 2002/0016465 A1 | 2/2002 | Walinsky et al. | |
| 2002/0016466 A1 | 2/2002 | Walinsky et al. | |
| 2002/0072538 A1 | 6/2002 | Chenard et al. | |
| 2002/0095056 A1 | 7/2002 | Cobley et al. | |

FOREIGN PATENT DOCUMENTS

| | | |
|---|---|---|
| EP | 0 901 997 A1 | 3/1999 |
| WO | WO 98/42643 A1 | 10/1998 |
| WO | WO 00/18708 A1 | 4/2000 |
| WO | WO 01/12574 A1 | 2/2001 |
| WO | WO 01/23088 A1 | 4/2001 |

OTHER PUBLICATIONS

Cao et al. "Ru–BICP–catalyzed asymmetric hydrogenation of aromatic ketones" CA 130:281548 (1999).*
Llorca et al. "Dichloro d–methionine–N,S–platinum II at 130K" CA 135:173144 (2001).*
Copy in copending case SN 158,560.*
U.S. patent application Ser. No. 10/057,826, Tucker et al., filed Jan. 24, 2002.

David J. Cross et al., "Rhodium Versus Ruthenium: Contrasting Behavior In The Asymmetric Transfer Hydrogenation Of A–Substituted Acetophenones", *Tetrahedron: Asymmetry,* 12:1801–1806 (2001).

Kai Rossen, "Ru– and Rh–Catalyzed Asymmetric Hydrogenations: Recent Surprises from an Old Reaction", *Angew. Chem. Int. Ed.,* 40:(24) 4611–4613 (2001).

Cao and Zhang, "Ru–BICP–Catalyzed Asymmetric Hydrogenation of Aromatic Ketones", *J. Org. Chem.,* 64:2127–2129 (1999).

Doucet et al., "Trans-[RuCl$_2$(phosphane)$_2$(1,2–diamine)] and Chiral trans–RuCl$_2$(diphosphane)(1,2–diamine): Shelf–Stable Precatalysts for the Rapid, Productive, and Stereoselective Hydrogenation of Ketones", *Angew. Chem. Int. Ed.,* 12:1703–07 (1998).

Grey et al., "Novel Anionic Phosphine Transition Metal Hydride Complexes and Their Application to the Catalytic Hydrogenation of Polar Organic Compounds,"Symposium on Homogeneous Catalysis Presented Before the Division of Petroleum Chemistry, Inc. American Chemical Society Houston Meeting, Mar. 23–28, 1980.

Hartmann and Chen, "Noyori's Hydrogenation Catalyst Needs a Lewis Acid Cocatalyst for High Activity," *Angew. Chem. Int. Ed.,* 19:3581–3585 (2001).

Hashiguchi et al., "Asymmetric Transfer Hydrogenation of Aromatic Ketones Catalyzed by Chiral Ruthenium (II) Complexes," *J. Am. Chem. Soc.,* 117:7562–7563 (1995).

Jiang, Y. et al., "A New Chiral Bis(oxazolinylmethyl)amine Ligand for Ru–Catalyzed Asymmetric Transfer Hydrogenation of Ketones," *J. Am. Chem. Soc.,* 120:3817–3818 (1998).

Lauhon and Szostak, "RNA Aptamers That Bind Flavin and Nicotinamide Redox Cofactors," *J. Am. Chem. Soc.,* 117:1246–1257 (1995).

Matsumura et al., "Asymmetric Transfer Hydrogenation of α,β–Acetylenic Ketones," *J. Am Chem. Soc.,* 119:8738–8739 (1997).

Mikami et al., "Asymmetric Activation/Deactivation of Recemic Ru Catalysts for Highly Enantioselective Hydrogenation of Ketonic Substrates," *Angew. Chem. Int. Ed.,* 20:3707–10 (2000).

Noyori and Ohkuma, "Asymmetric Catalysis by Architectural and Functional Molecular Engineering: Practical Chemo–and Stereoselective Hydrogenation of Ketones," *Angew. Chem. Int. Ed.,* 40:40–73 (2001).

(List continued on next page.)

*Primary Examiner*—Celia Chang
(74) *Attorney, Agent, or Firm*—Townsend and Townsend and Crew LLP

(57) ABSTRACT

The present invention provides a catalyst system and a process for the preparation of a nonracemic chiral alcohol by hydrogenation of a ketone using the catalyst system, wherein the catalyst system comprises ruthenium, a nonracemic chiral diphosphine ligand, an amino-thioether ligand, and a base.

10 Claims, No Drawings

OTHER PUBLICATIONS

Noyori, "Asymmetric Hydrogenation," *Acta Chemica Scandinavica*, 50:380–390 (1996).

Ohkuma et al., "Asymmetric Activation of Racemic Ruthenium (II) Complexes for Enantioselective Hydrogenation," *J. Am. Chem. Soc.*, 120:1086–1087 (1998).

Ohkuma et al., "Practical Enantioselective Hydrogenation of Aromatic Ketones," *J. Am. Chem. Soc.*, 117:2675–2676 (1995).

Ohkuma et al., "Asymmetric Hydrogenation of Alkenyl, Cyclopropyl, and Aryl Ketones, $RuCl_2$(xylbinap)(1,2-diamine) as a Precatalyst Exhibiting a Wide Scope," *J. Am. Chem. Soc.*, 120:13529–13530 (1988).

Ohkuma et al., "Asymmetric Hydrogenation of Cyclic α,β–Unsaturated Ketones to Chiral Allylic Alcohols," *Synlett, May 1997*, pp. 467–468.

Ohkuma et al., "General Asymmetric Hydrogenation of Hetero–aromatic Ketones," *Organic Letters*, 2:1749–1751 (2000).

Ohkuma et al., "Preferential Hydrogenation of Aldehydes and Ketones," *J. Am. Chem. Soc.*, 117:10417–10418 (1995).

Ohkuma et al., "Stereoselective Hydrogenation of Simple Ketones Catayzed by Ruthenium (II) Complexes," *J. Org. Chem.*, 61:4872–4873 (1996).

Püntener, K., et al., "New Efficient Catalysts for Enantioselective Transfer Hydrogenations, " *Tetrahendron Letters*, 45:8165–8168 (1996).

Sanchez–Delgado et al., "Chemistry and Catalytic Properties of Ruthenium and Osmium Complexes. 3. Development of Highly Active Systems for the Homogeneous Hydrogenation of Aldehydes and Ketones," *Inorg. Chem.*, 25:1106–1111 (1986).

Sanchez–Delgado and Ochoa, "Homogeneous Hydrogenation of Ketones to Alcohols With Ruthenium Complex Catalysts," *J. Organometallic Chem.*, 202: 427–434 (1980).

Sanchez–Delgado and Ochoa, "Homogeneous Hydrogenation of Aldehydes and Ketones by Use of Ruthenium Triphenylphosphine Complexes," *Journal Molecular Catalysis*, 6:303–305 (1979).

Sammakia and Stangeland, "Transfer Hydrogenation With Ruthenium Complexes of Chiral (Phosphinoferrocenyl)oxazolines," *J. Org. Chem.*, 62:6104–6105 (1997).

Takehara et al., "Amino Alcohol Effects on the Ruthenium(II)–Catalysed Asymmetric Transfer Hydrogenation of Ketones in Propan–2–ol," *Chem. Commun.*, pp. 233–234 (1996).

Yang et al., "Ruthenium(II) Complexes with New Tridentate Ligands Containing P,N,O Donor Atoms: Highly Efficient Catalysts for Transfer Hydrogenation of Ketones by Propan–2–ol," *J. Chem. Soc., Chem Commun* pp. 1721–1722 (1995) 12.

Abdur–Rashid et al., "Catalytic cycle for the asymmetric hydrogenation of prochiral ketones to chiral alcohols: direct hydride and proton transfer from chiral catalysts trans–Ru(H)$_2$(diphosphine)(diamine) to ketones and direct addition of dihydrogen to the resulting hydridoamido complexes" J. Am. Chem. Soc. 123:7473–7474 (2001).

Winter et al., "Trapping of butatrienylidine complexes with functional ternary amines" CA 1997:487599 (1997).

* cited by examiner

US 6,806,378 B2

PROCESS FOR PREPARING NONRACEMIC CHIRAL ALCOHOLS

CROSS-REFERENCES TO RELATED APPLICATIONS

This application is a continuation-in-part of U.S. patent application Ser. No. 10/057,826, filed Jan. 24, 2002, incorporated herein by reference in its entirety. This application is also related to co-filed U.S. patent applications Ser. No. 10/158,559 ("Process for Preparing Nonracemic Chiral Alcohols"), and Ser. No. 10/158,160 ("Process for Preparing Nonracemic Chiral Alcohols"), incorporated herein by reference in their entireties.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

FIELD OF THE INVENTION

This invention relates generally to preparing nonracemic chiral alcohols. It more particularly relates to preparing nonracemic chiral alcohols by hydrogenation of ketones using transition metal catalysts comprising nonracemic chiral ligands. Nonracemic chiral alcohols are useful as pharmaceuticals and other bioactive products and as intermediates for the preparation of such products.

BACKGROUND OF THE INVENTION

Ketones can be converted to racemic chiral alcohols by hydrogenation using certain catalyst systems of ruthenium, a phosphine ligand, a 1,2-diamine, and an alkaline base. Aromatic and heteroaromatic ketones can be hydrogenated to nonracemic chiral alcohols by using certain catalyst systems of ruthenium, an appropriate enantiomeric diphosphine ligand, an enantiomeric 1,2-diamine, and an alkaline base. Angew. Chem. Int. Ed., vol. 40, (2001), 40–73 (a review with 211 references); U.S. Pat. No. 5,763,688; J. Am. Chem. Soc., vol. 117 (1995), 2675–2676; J. Org. Chem., vol. 64 (1999), 2127–2129. Others have noted that such ketones can be hydrogenated to nonracemic chiral alcohols using related catalyst systems formed with a racemic chiral 1,2-diamine. In their catalyst system, the active diastereomeric ruthenium catalyst is formed with the enantiomeric atropisomeric diphosphine ligand and the "matched" enantiomer of the racemic chiral 1,2-diamine. Interestingly, the diastereomeric ruthenium complex with the "unmatched" enantiomer of the racemic chiral 1,2-diamine, if it is formed, is relatively inactive. Angew. Chem. Int. Ed., vol. 40, (2001), 40–73; European Patent Application 901 997; J. Am. Chem. Soc., vol. 120 (1998), 1086–1087. A catalyst system of ruthenium, the atropisomeric diphosphine (S)-2,2'-bis-(diphenylphosphino)-1,1'-binaphthyl (S-BINAP), achiral ethylene diamine, and potassium hydroxide in isopropanol is reported to hydrogenate 1'-acetonaphthone to (R)-1-(1-naphthyl)-ethanol in 57% enantiomeric excess. The corresponding catalyst system having enantiomeric (S,S)-1,2-diphenylethylenediamine instead of achiral ethylene diamine is reported to hydrogenate 1'-acetonaphthone under the same conditions to (R)-1-(1-naphthyl)ethanol in 97% enantiomeric excess. Angew. Chem. Int. Ed., vol. 40, (2001), 40–73; J. Am. Chem. Soc., vol. 117 (1995), 2675–2676.

An attempt to provide a catalyst system of ruthenium, the atropisomeric diphosphine S-BINAP, enantiomeric (S,S)-1,2-diphenylethylenediamine, and 1,8-diaza-bicyclo[5.4.0]undec-7-ene as the base (in the place of the alkali base used in the references discussed above) gave no catalytic activity for the hydrogenation of acetophenone. The addition of selected alkali salts of tetrakis[3,5-bis(trifluoromethyl)phenyl]borate to this attempted catalyst system provided catalytic activity for the hydrogenation of acetophenone to nonracemic 1-phenethanol. The investigators conclude that alkali metal cations are required for the activity of this catalyst system. Angew. Chem. Int. Ed., vol. 40, (2001), 3581–3585.

BRIEF SUMMARY OF THE INVENTION

The present invention provides a catalyst system as well as a process for the preparation of a nonracemic chiral alcohol by hydrogenation of a ketone using the catalyst system. The catalyst system comprises ruthenium, a nonracemic chiral diphosphine ligand, an amino-thioether ligand, and a base. Surprisingly, and in contrast to teaching in the art, a chiral diamine ligand is not required to obtain highly enantioselective hydrogenation of a ketone to a nonracemic chiral alcohol when using a catalyst system comprising ruthenium, a nonracemic chiral diphosphine ligand, an amine ligand and a base. Accordingly, the present invention provides methods for the highly enantioselective hydrogenation of a ketone to a nonracemic chiral alcohol using an amino-thioether ligand, with a catalyst system also comprising ruthenium, a nonracemic chiral diphosphine ligand, and a base.

In one group of embodiments the base is selected from alkylamidines, alkylguanidines, aminophosphazenes, and proazaphosphatranes.

BRIEF DESCRIPTION OF THE DRAWINGS

Not applicable

DETAILED DESCRIPTION OF THE INVENTION

Unless otherwise stated, the following terms used in the specification and claims have the meanings given below:

As used herein, the term "treating", "contacting" or "reacting" refers to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. "Side-reaction" is a reaction that does not ultimately lead to a production of a desired product.

"Alkyl" means a linear saturated monovalent hydrocarbon radical or a branched saturated monovalent hydrocarbon radical or a cyclic saturated monovalent hydrocarbon radical, having the number of carbon atoms indicated in the prefix. For example, $(C_1-C_6)$alkyl is meant to include methyl, ethyl, n-propyl, 2-propyl, tert-butyl, pentyl, cyclopentyl, cyclohexyl and the like. For each of the definitions herein (e.g., alkyl, alkenyl, alkoxy, aralkyloxy), when a prefix is not included to indicate the number of main chain carbon atoms in an alkyl portion, the radical or portion thereof will have twelve or fewer main chain carbon atoms. A divalent alkyl radical refers to a linear saturated divalent hydrocarbon radical or a branched saturated divalent hydrocarbon radical having the number of carbon atoms indicated in the prefix. For example, a divalent $(C_1–C_6)$alkyl is meant to include methylene, ethylene, propylene, 2-methylpropylene, pentylene, and the like.

"Alkenyl" means a linear monovalent hydrocarbon radical or a branched monovalent hydrocarbon radical having the number of carbon atoms indicated in the prefix and containing at least one double bond. For example, $(C_2–C_6)$ alkenyl is meant to include, ethenyl, propenyl, and the like.

"Alkynyl" means a linear monovalent hydrocarbon radical or a branched monovalent hydrocarbon radical containing at least one triple bond and having the number of carbon atoms indicated in the prefix. For example, $(C_2–C_6)$alkynyl is meant to include ethynyl, propynyl, and the like.

"Alkoxy", "aryloxy", "aralkyloxy", or "heteroaralkyloxy" means a radical —OR where R is an alkyl, aryl, aralkyl, or heteroaralkyl respectively, as defined herein, e.g., methoxy, phenoxy, benzyloxy, pyridin-2-ylmethyloxy, and the like.

"Aryl" means a monocyclic or bicyclic aromatic hydrocarbon radical of 6 to 12 ring atoms which is substituted independently with one to four substituents, preferably one, two, or three substituents selected from alkyl, alkenyl, alkynyl, halo, nitro, cyano, hydroxy, alkoxy, amino, acylamino, mono-alkylamino, di-alkylamino and heteroalkyl. More specifically the term aryl includes, but is not limited to, phenyl, biphenyl, 1-naphthyl, and 2-naphthyl, and the substituted derivatives thereof.

"Aralkyl" refers to a radical wherein an aryl group is attached to an alkyl group, the combination being attached to the remainder of the molecule through the alkyl portion. Examples of aralkyl groups are benzyl, phenylethyl, and the like.

"Heteroalkyl" means an alkyl radical as defined herein with one, two or three substituents independently selected from cyano, alkoxy, amino, mono- or di-alkylamino, thioalkoxy, and the like, with the understanding that the point of attachment of the heteroalkyl radical to the remainder of the molecule is through a carbon atom of the heteroalkyl radical.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one to four substituents, preferably one or two substituents, selected from alkyl, alkenyl, alkynyl, halo, nitro, cyano, hydroxy, alkoxy, amino, acylamino, mono-alkylamino, di-alkylamino and heteroalkyl. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyridazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, and the substituted derivatives thereof.

"Hydrocarbyl" is used herein to refer to an organic radical, that can be an alkyl, alkenyl, alkynyl, aryl, aralkyl, heteroalkyl or heteroaryl radical, or a combination thereof which is optionally substituted with one or more substituents generally selected from the groups noted above.

In a general sense, the present invention provides a method for the preparation of a chiral alcohol of formula II (shown without stereochemistry) from a ketone of formula I. Suitable ketones for use in the present invention are those wherein $R^1$ and $R^2$ are different, and optionally, one or both of $R^1$ and $R^2$ have a chiral center.

The symbols $R^1$ and $R^2$ in formulas I and II each independently represent a hydrocarbyl group that can be an acyclic, cyclic, or heterocyclic hydrocarbyl group, or a combination thereof. Additionally, each of the hydrocarbyl groups $R^1$ and $R^2$ can be saturated or unsaturated, including components defined above as alkyl, heteroalkyl, aryl, heteroaryl, aralkyl, alkenyl, and alkynyl groups, as well as combinations thereof. Still further, each of $R^1$ and $R^2$ can be optionally substituted with one or more substituents that do not interfere with the reaction chemistry of the invention. In some embodiments, $R^1$ and $R^2$ are linked together in a cyclic structure. In a preferred combination of $R^1$ and $R^2$, $R^1$ is an optionally substituted alkyl group and $R^2$ is an optionally substituted aryl or heteroaryl group.

$R^1$ and $R^2$ can also be, independently, chiral or achiral. As used herein, however, the adjective "chiral" in the term "chiral alcohol", specifically refers to the chirality at the carbon atom bearing each of $R^1$ and $R^2$, which chirality is produced by the hydrogenation of the keto group at that center. The term is not meant to refer to the chirality that may be present in either $R^1$ or $R^2$.

The ruthenium, nonracemic chiral diphosphine ligand, and amino-thioether ligand components of the catalyst system can be provided to the reaction mixture individually to form the reactive catalyst complex in situ or they can be provided as preformed complexes. Preformed complexes of ruthenium with the diphosphine ligand, or the amino-thioether ligand, or both can be used.

Examples of preformed complexes of the ruthenium with the diphosphine ligand include complexes represented by the formula $RuX_2LY_n$, wherein X represents a halogen atom or pseudo-halide group, preferably chloride or bromide, L represents the diphosphine ligand, Y represents a weakly coordinating neutral ligand, and n is an integer from 1 to 5. Examples of Y include trialkylamines, for examples triethylamine and tetramethylethylenediamine, and tertiary amides, for example dimethylformamide. Such complexes can be prepared by the reaction of the diphosphine ligand with a complex of the formula $[RuX_2(arene)]_2$, wherein examples of the arene include benzene, p-cymene, 1,3,5-trimethylbenzene, and hexamethylbenzene, in a solvent comprising Y.

Examples of preformed complexes of the ruthenium with both the diphosphine ligand and amino-thioether ligand include complexes represented by the formula $RuX_2LA$, wherein A represents the amino-thioether ligand. Such complexes can be prepared by the reaction of the aminothioether with a complex of the formula $RuX_2LY_n$ as described above.

The ruthenium component of the catalyst system, whether provided to the reaction mixture separately from the other components or used to form a preformed complex with the diphosphine ligand, the amino-thioether ligand, or both, can be provided by any ruthenium salt or complex capable of forming the active catalyst system in combination with the diphosphine ligand, the amino-thioether ligand, and the base. This can be determined by routine functional testing for ketone hydrogenation activity and enantioselectivity in the manner shown in the Examples. A preferred source of the ruthenium component is a complex of the formula $[RuX_2(arene)]_2$ as defined above.

Suitable nonracemic chiral diphosphine ligands for the present invention are bis-tertiary phosphines of the general formula $R^3R^4PR^aPR^5R^6$, wherein $R^3$, $R^4$, $R^5$, and $R^6$ are hydrocarbyl radicals, which may be the same or different, and $R^a$ is a hydrocarbyl diradical, any of which may be optionally linked in one or more cyclic structures. Suitable hydrocarbyl groups $R^3$, $R^4$, $R^5$, $R^6$, and diradicals thereof for $R^a$, include acyclic, cyclic, or heterocyclic hydrocarbyl groups, or combinations thereof. Additionally, each of the hydrocarbyl groups $R^3$, $R^4$, $R^5$, $R^6$ and $R^a$ can be saturated or unsaturated, including components defined above as alkyl, heteroalkyl, aryl, heteroaryl, aralkyl, alkenyl, and alkynyl groups, as well as combinations thereof. Still further, each of $R^3$, $R^4$, $R^5$, $R^6$ and $R^a$ can can be optionally substituted with one or more substituents that do not undesirably affect the reaction chemistry of the invention.

The chirality of the diphosphine ligand may reside in one or more of the hydrocarbyl groups $R^3$, $R^4$, $R^5$, $R^6$, in the bridging hydrocarbyl radical $R^a$, at phosphorus when two hydrocarbyl radicals on phosphorus are different ($R^3 \neq R^4$, or $R^5 \neq R^6$, or both), or combinations thereof. Chirality in the bridging hydrocarbyl diradical $R^a$ may be due to the presence of one or more stereogenic carbon atoms or due to atropoisomerism.

Illustrative examples of nonracemic chiral diphosphines are the enantiomers of 2,2'-bis(diphenyl-phosphino)-1,1'-binaphthyl (BINAP), BINAP derivatives having one or more alkyl groups or aryl groups connected to one or both naphthyl rings, BINAP derivatives having 1–5 alkyl substituents on the phenyl rings bonded to phosphorus, for example 2,2'-bis-(di-p-tolylphosphino)-1,1'-binaphthyl (TolBINAP), 5,6,7,8,5',6',7',8'-octahydro-BINAP ($H_8$BINAP), 2,2'-bis(dicyclohexylphosphino)-6,6'-dimethyl-1,1'-biphenyl (BICHEP), 2,2'-bis(diphenylphosphino)-6,6'-dimethoxy-1,1'-biphenyl (MeOBIPHEP), 1-[1,2-bis-(diphenylphosphino)ferrocenyl] ethyldimethylamine (BPPFA), 2,3-bis(diphenyl-phosphino) butane (CHIRAPHOS), 1-cyclohexyl-1,2-bis (diphenylphosphino)ethane (CYCPHOS), 1-substituted 3,4-bis(diphenyl-phosphino)pyrolidine (DEGPHOS), 2,3-O-isopropylidene-2,3-dihydroxy-1,4-bis(diphenylphosphino) butane (DIOP), 1,2-bis[(o-methoxyphenyl) phenylphosphino]ethane (DIPAMP), 2,5-disubstituted 1,2-bis(phospholano)benzenes (DuPHOS), for example 1,2-bis (2,5-dimethylphospholano)-benzene (Me-DuPHOS), substituted 1,2-bis(phospholano)ethylenes (BPE), for example 1,2-bis(2,5-dimethylphospholano)ethylene (Me-BPE), 5,6-bis(diphenylphosphino)-2-norbornene (NORPHOS), N,N'-bis-(diphenylphosphino)-N,N'-bis(1-phenylethyl)ethylene-diamine (PNNP), 1,2-bis-(diphenylphosphino)propane (PROPHOS), 2,4-bis (diphenyl-phosphino)pentane (SKEWPHOS), [6,7,8,9-tetrahydro-dibenzo[b,d]-[1,6]-dioxecin-1,14-diyl]-bis (diphenylphosphine) (C4-TunaPhos), 3,4-O-isopropylidene-3,4-dihydroxy-2,5-bis-(diphenylphosphino)hexane (DIOP*), 1,2-bis {4,5-dihydro-3H-dinaphtho-[2, 1-c: 1',2'-e]-phosphino}benzene (BINAPHANE), 1,1'-bis-{4,5-dihydro-3H-dinaphtho[2,1-c: 1',2'-e]-phosphino}ferrocene (f-BINAPHANE), 1,2-bis-[3,4-O-isopropylidene-3,4-dihydroxy-2,5-dimethylphospholanyl]benzene (Me-KetalPhos), 1,1'-bis[3,4-O-isopropylidene-3,4-dihydroxy-2,5-dimethyl-phospholanyl]ferrocene (Me-f-KetalPhos), 2,2'-bis(diphenyl-phosphino)-1,1'-dicyclopentane (BICP), 1,2-bis-{2,5-disubstituted-7-phosphabicyclo[2.2.1]-hept-7-yl}benzenes (PennPhos), for example 1,2-bis-{2,5-dimethyl-7-phosphabicyclo[2.2.1]-hept-7-yl}benzene (Me-PennPhos) and 1,2-bis-{2,5-diisopropyl-7-phosphabicyclo [2.2.1]-hept-7-yl}benzene (iPr-PennPhos), and 1,2-bis {1-phosphatricyclo[3.3.0.0]undecan-1-yl}-benzene (C5-Tricyclophos), and equivalents thereto that are recognized by those skilled in the art.

Preferred nonracemic diphosphine ligands comprise a 2,2'-bis-(diorgano-phosphino)-1,1'-bis(cyclic) structure, wherein each cycle of the bis(cyclic) structure comprises three to eight carbon atoms, and wherein the 1, 1', 2, and 2' carbon atoms in the bis(cyclic) structure are saturated. These ligands are described in detail in U.S. Pat. No. 6,037,500, incorporated herein by reference. The preferred nonracemic diphosphine ligands comprising a 2,2'-bis-(diorgano-phosphino)-1,1'-bis(cyclic) structure are of the formulas III and IV and their enantiomers, in which m=1 to 6 and wherein each cycle of the bis(cyclic) structure may be unsubstituted as shown in formulas III and IV or further substituted with one or more substituents chosen from hydrocarbyl substituents and heteroatom containing substituents that do not interfere with the ketone hydrogenation chemistry, and wherein R' is a substituted or unsubstituted hydrocarbyl group selected from alkyl groups and aryl groups.

III

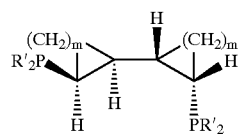

IV

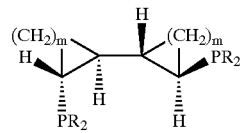

Particularly preferred nonracemic diphosphine ligands are of the formula V and its enantiomer, wherein Ar is an aryl group.

V

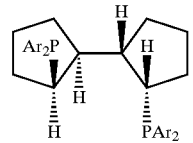

Preferred aryl groups in formula V are phenyl (the BICP ligand) and mono-, di-, and trialkyl-phenyl, particularly wherein alkyl is methyl, for example 2,2'-bis[di(3,5-dimethylphenyl)phosphino]-1,1'-dicyclopentane (3,5-Me$_8$BICP).

Suitable amino-thioether ligands for the present invention are of the general formula $H_2NR^cSR^7$, wherein $R^7$ is a hydrocarbyl radical and $R^c$ is a hydrocarbyl diradical and which may be optionally linked in a cyclic structure. Suitable hydrocarbyl groups $R^7$ and diradicals thereof for $R^c$ include acyclic, cyclic, and heterocyclic hydrocarbyl groups, include saturated and unsaturated hydrocarbyl groups, include alkyl, heteroalkyl, aryl, heteroaryl, aralkyl, alkenyl, and alkynyl groups, and can be optionally substituted with one or more substituents that do not undesirably the reaction chemistry of the invention. The amino-thioether ligand may be achiral, racemic chiral, or nonracemic chiral, preferably achiral.

Preferred amino-thioether ligands are selected from 2-(alkylthio)ethylamines, 2-(alkylthio)anilines, and equivalents thereto that are recognized by those skilled in the art. Most preferred are 2-(alkylthio)anilines. Preferably the alkyl group therein is selected from $C_1$ to $C_4$ alkyl groups. Most preferred are methyl and ethyl. Illustrative examples include 2-(methylthio)aniline and 2-(ethylthio)aniline.

Suitable bases include basic inorganic and organic salts, preferably selected from basic salts comprising a cation selected from an alkali metal cation, an alkaline earth cation, and quaternary ammonium cation and a basic anion selected from hydroxide and alkoxide anions. Examples include lithium, sodium, potassium, and quaternary ammonium salts of hydroxide, methoxide, ethoxide, isopropoxide, and t-butoxide.

In a further inventive embodiment of the invention, the base is selected from alkylguanidines, aminophosphazenes, proazaphosphatranes, and alkylamidines. In this embodiment, the base is preferably selected from alkylguanidines, aminophosphazenes, and proazaphosphatranes. In this embodiment, the base is most preferably selected from alkylguanidines.

Suitable alkylguanidines have the general formula VI, wherein $R^8$, $R^9$, $R^{10}$, $R^{11}$, and $R^{12}$ are independently selected from hydrogen and alkyl groups, with the proviso that at least one of $R^8$, $R^9$, $R^{10}$, $R^{11}$, and $R^{12}$ is an alkyl group.

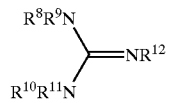

VI

Preferably the alkylguanidine comprises two alkyl groups, more preferably three alkyl groups, even more preferably four alkyl groups, and most preferably five alkyl groups. Any of the alkyl groups $R^8$, $R^9$, $R^{10}$, $R^{11}$, and $R^{12}$ may be optionally linked in one or more cyclic structures. An illustrative example of a suitable tetraalkylguanidine base is 1,5,7-triazabicyclo[4.4.0]dec-5-ene and tetramethylguanidine. Illustrative examples of suitable pentalkylguanidines are 7-methyl-1,5,7-triazabicyclo[4.4.0]dec-5-ene and tetramethyl-2-t-butylguanidine.

Suitable aminophosphazenes have the general formula VII, wherein $R^{13}$ is selected from hydrogen and alkyl groups, $R^{14}$ is an alkyl group and the two $R^{14}$ groups on each $-NR^{14}_2$ group may optionally be linked in a cyclic structure, and x is an integer from zero to three.

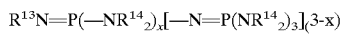

VII

Illustrative examples of suitable aminophosphazenes include N,N,N',N',N",N"-hexa-methyl-phosphorimidic triamide ($R^{13}$=H, $R^{14}$=methyl, x=3), N'''-t-butyl-N,N,N',N',N", N"-hexamethyl-phosphorimidic triamide ($R^{13}$=t-butyl, $R^{14}$=methyl, x=3), (t-butyl-imino)-tris(pyrrolidino)-phosphorane ($R^{13}$=t-butyl, $-NR^{14}_2$=pyrrolidino, x=3), N'''-[N-ethyl-P,P-bis-(dimethyl-amino)phosphinimyl]-N,N,N',N',N",N"-hexamethyl-phosphorimidic triamide ($R^{13}$=ethyl, $R^{14}$=methyl, x=2), and t-butyl-tris[tris(dimethyl-amino)-phosphoranylidene]phosphorimidic triamide ($R^{13}$=t-butyl, $R^{14}$=methyl, x=0).

Suitable proazaphosphatranes are described in U.S. Pat. No. 5,051,533 and have the general formula VIII, wherein $R^{15}$, $R^{16}$, and $R^{17}$ are independently selected from hydrogen and alkyl groups.

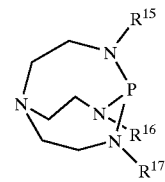

VIII

Preferably $R^{15}$, $R^{16}$, and $R^{17}$ are selected from $C_1$ to $C_8$ alkyl groups, most preferably methyl. An illustrative preferred proazaphosphatrane is 2,8,9-trimethyl-2,5,8,9-tetraaza-1-phosphabicyclo[3.3.3]undecane ($R^{15}=R^{16}=R^{17}=$ methyl).

Suitable alkylamidines have the general formula IX wherein $R^{18}$, $R^{19}$, and $R^{20}$ are independently selected from alkyl groups and $R^{21}$ is selected from hydrogen and alkyl groups. Preferably, $R^{21}$ is selected from alkyl groups.

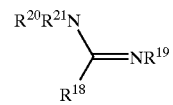

IX

Any of the alkyl groups $R^{18}$, $R^{19}$, $R^{20}$, and $R^{21}$ may be optionally linked in one or more cyclic structures. An illustrative example of a suitable alkylamidine base is 1,5-diazabicyclo[4.3.0]non-5-ene.

The components of the catalyst system are each present in catalytic amounts, meaning less than stoichiometric relative to the ketone reactants. The minimum amount of the catalyst system relative to the ketone reactant may depend on the activity of the specific catalyst system composition, the specific ketone to be reacted, the hydrogen pressure, the gas-liquid mixing characteristics of the reaction vessel, the reaction temperature, the concentrations of the reactants and catalyst system components in the solution, and the maximum time allowed for completion of the reaction, and can be readily determined by routine experimentation. In typical embodiments, the mole ratio of the ruthenium component of the catalyst system to the ketone reactant is in the range from about 1/100 to about 1/100,000, preferably in the range from about 1/500 to about 1/10,000.

The mole ratio of the nonracemic diphosphine ligand to the ruthenium in the catalyst system is typically in the range from about 0.5 to about 2.0, preferably from about 0.8 to about 1.2, and most preferably is about 1. The mole ratio of the amino-thioether ligand to the ruthenium in the catalyst system is typically in the range from about 1 to about 50, and preferably from about 5 to about 20. The mole ratio of the base to the ruthenium in the catalyst system is typically in the range from about 1 to about 100, and preferably from about 5 to about 50.

The hydrogenation reaction may be conducted without solvent when the ketone itself is a liquid at the reaction temperature and capable of dissolving the catalyst system. More typically, the hydrogenation reaction is conducted in a solvent system that is capable of dissolving the catalyst system and is reaction-inert. The term solvent system is used to indicate that a single solvent or a mixture of two or more solvents can be used. The term reaction-inert it used to mean that the solvent system does not react unfavorably with the reactants, products, or the catalyst system. It does not mean that the solvent does not participate productively in the desired reaction. For example, while not wishing to be bound by theory, it is believed that when the base is selected from alkylguanidines, aminophos-phazenes, or proazaphosphatranes and the solvent is selected from alcohol solvents, the alcohol solvent levels the base. That is, these bases deprotonate the alcohol to form an alkoxide base in the reaction solution.

The solvent system need not bring about complete solution of the ketone reactant or the chiral alcohol product. The ketone reactant may be incompletely dissolved at the beginning of the reaction or the chiral alcohol product may be incompletely dissolved at the end of the reaction, or both.

Representative solvents are aromatic hydrocarbons such as benzene, toluene, xylene; aliphatic hydrocarbons such as pentane, hexane, heptane; halogen-containing hydrocarbon solvents such as dichloromethane and chlorobenzene; alkyl ethers, polyethers, and cyclic ethers such as methyl-t-butylether, dibutylether, diethoxymethane, 1,2-dimethoxyethane, and tetrahydrofuran; ester solvents such as ethyl acetate, organic solvents containing heteroatoms such as acetonitrile, DMF and DMSO; and alcohol solvents such as methanol, ethanol, 2-propanol, t-butanol, benzyl alcohol and the like; and mixtures thereof. Preferably, the solvent system comprises an alcohol solvent. Most preferably, the alcohol solvent is 2-propanol.

In typical embodiments, the reaction is suitably conducted at a temperature from about −30° C. to about 100° C., more typically from about 0° C. to about 50° C., and most typically from about 20° C. to about 40° C.

The terms "hydrogenating" and "hydrogenation" refer to reacting the ketone with a source of hydrogen atoms under appropriate conditions so that two hydrogen atoms are added to the carbonyl group of the ketone to produce the hydroxyl group of the chiral alcohol. The source of hydrogen atoms may be molecular hydrogen ($H_2$), a hydrogen donating organic or inorganic compound, or mixtures thereof. Preferably the source of hydrogen atoms includes molecular hydrogen. Hydrogen donating compounds are compounds capable of donating hydrogen atoms via the action of the catalyst system. Compounds capable of donating hydrogen atoms for transfer hydrogenation reactions using ruthenium catalysts are known in the art, and include alcohols such as methanol, ethanol, n-propanol, isopropanol, butanol and benzyl alcohol, formic acid and salts thereof, unsaturated hydrocarbons and heterocyclic compounds having in part a saturated C—C bond such as tetralin, cyclohexane, and cyclohexadiene, hydroquinone, phosphorous acid, and the like. Among hydrogen donating compounds, alcohols are preferred and isopropanol is most preferred.

The hydrogen pressure in the reaction is typically at least about 1 atm, and typically in the range from about 1 atm to about 100 atm. More typically, the hydrogen pressure is in the range from about 5 atm to about 20 atm.

The reaction rate and time to completion are dependent on the identities of the ketone reactant and the catalyst components, their absolute concentrations and relative ratios, the temperature, the hydrogen pressure, the gas-liquid mixing provided, and the other reaction conditions. Typically, the reaction is allowed to continue for sufficient time to complete the conversion of the ketone reactant. For typical ketone reactants, using the preferred catalyst systems described and the preferred reaction conditions described herein, the reaction is typically completed in a period of time in the range from about a few minutes to about 24 hours, more typically in the range from about 1 hour to about 10 hours.

The nonracemic chiral alcohol product has, by definition, a stereomeric excess greater than zero. In preferred embodiments, the nonracemic chiral alcohol is formed in at least about 50% stereomeric excess, more preferably at least about 60%, still more preferably at least about 70%, still again more preferably at least about 80%, and most preferably at least about 90%. These stereomeric excesses refer to the chirality at the hydroxyl-bearing carbon of the alcohol group generated by the hydrogenation of the ketone group. When the ketone is achiral, the chiral alcohol can be one of two enantiomers, and the enantiomer excess (e.e.) is the measure of stereomeric excess. When the ketone reactant is already chiral, the chiral alcohol product is a diastereomer, and diastereomeric excess (d.e.) is the formally appropriate measure of stereomeric excess. Accordingly, the term "nonracemic diastereomer" when used to refer to a nonracemic chiral alcohol product, refers to a product with an excess of one diastereomer vs. its diastereomer with the opposite chirality at the hydroxyl-bearing carbon. Preferably, the nonracemic diastereomer is produced in at least about 50% d.e., more preferably at least about 60% d.e., still more preferably at least about 70% d.e., still again more preferably at least about 80% d.e., and most preferably at least about 90% d.e.

EXAMPLES OF THE INVENTION

Without further elaboration, it is believed that one skilled in the art can, using the preceding description, utilize the present invention to its fullest extent. The following specific examples are intended merely to illustrate the invention and not to limit the scope of the disclosure or the scope of the claims in any way whatsoever.

Preparation 1

Preparation of [$RuCl_2$(R,R,R,R-BICP)(DMF)n]: To 7.5 mg (30 microgram-atom Ru) [$RuCl_2$(benzene)]$_2$ and 16.2 mg (32 micromole) (R,R,R,R)-2,2'-bis-(diphenylphosphino)-1,1'-dicyclopentane (R,R,R,R-BICP) in a 200 mL Schlenk flask under nitrogen was added 10 mL anhydrous, deaerated dimethylformamide (DMF). The resulting orange solution was heated at 130° C. for 30 minutes, then evaporated to dryness at 130° C. under vacuum (10 mmHg). The resulting orange-red solid residue, comprising [$RuCl_2$(R,R,R,R-BICP)(DMF)n], was further dried at 80° C. under vacuum for at least an additional hour. A stock solution of 250 micromolar [$RuCl_2$((R,R,R,R-BICP)(DMF)n] in isopropanol was prepared by dissolving the solid residue in 120 mL anhydrous, deaerated isopropanol and stored under nitrogen.

This general procedure was used for the preparation of the other [$RuCl_2$(diphosphine)(DMF)n] complexes and the solutions thereof used in the following Examples.

Example 1

This Example illustrates the process of the invention wherein acetophenone is hydrogenated to nonracemic 1-phenethanol using a ruthenium catalyst system comprising a nonracemic diphosphine ligand comprising a 2,2'-bis (diorganophosphino)-1,1'-bis(cyclic) structure, an amino-thioether ligand and an alkylguanidine base.

In a dry nitrogen-filled glovebox, a 20-mL glass reaction vial was charged with 5 mL 250 micromolar (1.25 micromole) [RuCl$_2$((R,R,R,R-BICP)(DMF)n] in isopropanol, 5 mL isopropanol, and 125 microliter 0.1M (12.5 micromole) 2-(ethylthio)aniline in isopropanol. After stirring for several minutes, 73 microliter (625 micromole) acetophenone was added, followed by 125 microliter 0.1 M (12.5 micromoles) tetramethyl-2-t-butylguanidine in isopropanol. The glass reaction vial containing the resulting mixture was sealed in an autoclave, which was then removed from the glovebox. The gas phase in the autoclave was replaced by hydrogen at 18 bar and the reaction mixture was stirred at room temperature for 6 hours under 17–18 bar hydrogen. After releasing the hydrogen pressure, 1 mL of the resulting reaction solution was eluted through a short column of silica gel with 9 mL methanol. Chiral gas chromatographic analysis of the eluate showed 100% conversion of the ketone to give S-1-phenethanol with 83% e.e.

Example 2

This Example illustrates the process of the invention wherein acetophenone is hydrogenated to nonracemic 1-phenethanol using a ruthenium catalyst system comprising a nonracemic diphosphine ligand comprising a 2,2'-bis(diorganophosphino)-1,1'-bis(cyclic) structure, an amino-thioether ligand and an alkoxide base.

The procedure was the identical to Example 1 with the exemptions that 63 microliter 0.2 M (12.5 micromoles) sodium isopropoxide in isopropanol was used instead of the tetramethyl-2-t-butylguanidine solution. The analysis showed 100% conversion of the acetophenone to give S-1-phenethanol with 83% e.e.

Comparative Example 1

This Example shows the result of omitting the amino-thioether ligand from the catalyst system.

The procedure was identical to Example 2 with the exception that the 2-(ethylthio)aniline was omitted. The analysis showed 35% conversion of the acetophenone to give S-1-phenethanol with 32% e.e.

By comparison, Example 2 shows that substantially greater activity (conversion) and enantioselectivity (e.e.) are provided by the catalyst system comprising an amino-thioether ligand.

Comparative Example 2

This Example shows the result of substituting an amino-thiol for the amino-thioether in the inventive catalyst system.

The procedure was identical to Example 2 with the exceptions that an equal molar amount of 2-mercaptoaniline was substituted for the 2-(ethylthio)aniline, and 37.5 micromoles of sodium isopropoxide in isopropanol was added instead of 12.5 micromoles. After 6 hours reaction time, the analysis showed the conversion of the acetophenone to be less than 1%.

By comparisons to Example 2 and Comparative Example 1, this shows that an amino-thiol severely inhibits the activity of the ruthenium catalyst.

Comparative Example 3

This Example shows the result of omitting the base from the catalyst system.

The procedure was identical to Example 2 with the exception that the sodium isopropoxide solution was omitted. The analysis showed no reaction occurred.

By comparison, Examples 1 and 2 show that the activity for ketone hydrogenation is provided by the catalyst system comprising a base.

Examples 3 and 4

These Examples illustrate the transfer hydrogenation of acetophenone to nonracemic 1-phenethanol using a using isopropanol as the hydrogen donating compound in the absence of hydrogen.

The procedures were identical to Examples 1 and 2, respectively, with the exception that the reaction mixtures were stirred for 12 hours with a gas phase of nitrogen instead of 6 hours with a gas phase of hydrogen. The analyses showed, respectively, 11% and 17% conversions of the acetophenone to give S-1-phenethanol with 86% and 83% e.e.

By comparison, Examples 1 and 2 show that the activity of the catalyst system is greater for hydrogenation using molecular hydrogen than for transfer hydrogenation using isopropanol as the sole source of hydrogen atoms, though the enantioselectivity provided by the nonracemic catalyst is comparable.

Examples 5 and 6

These Examples illustrate the process of the invention for hydrogenation of 2-acetylthiophene to nonracemic 1-(2-thienyl)ethanol using catalyst systems of the invention.

The procedures were identical to Examples 1 and 2, respectively, with the exception that 68 microliter (625 micromole) 2-acetylthiophene was reacted instead of the acetophenone. The analyses showed 100% conversion of the 2-acetylthiophene to give S-1-(2-thienyl)ethanol with 78% e.e. in both reactions.

Examples 7–30

These Examples show the process of the invention for hydrogenation of various ketones to nonracemic chiral using catalyst systems of the invention.

The procedure was identical to Example 2 with the exceptions that 625 micromole of the ketone shown in Table 1 was reacted instead of the acetophenone, 125 microliter of the 0.2 M (25 micromoles) sodium isopropoxide in isopropanol was added instead of 63 microliter, and the reaction mixtures were stirred for 12 hours. In each example, the analysis showed the conversion of the ketone was 100%. The ketone, the chirality of its nonracemic chiral alcohol product, and its e.e. are given in Table 1.

TABLE 1

| Example | ketone | % e.e. (R/S) |
| --- | --- | --- |
| 7 | 1-acetonaphthone | 80 (S) |
| 8 | 3-acetylpyridine | 72 (unknown) |
| 9 | 2-acetyl-3-methylthiophene | 69 (S) |
| 10 | 3-acetyl-2,5-dimethylthiophene | 90 (S) |
| 11 | propiophenone | 87 (S) |
| 12 | 4'-methylacetophenone | 86 (S) |

TABLE 1-continued

| Example | ketone | % e.e. (R/S) |
|---|---|---|
| 13 | 2'-methoxyacetophenone | 66 (S) |
| 14 | 4'-methoxyacetophenone | 87 (S) |
| 15 | 4'-fluoroacetophenone | 82 (S) |
| 16 | 4'-isobutylacetophenone | 84 (S) |
| 17 | 2'-methylacetophenone | 79 (S) |
| 18 | 2-acetonaphthone | 83 (S) |
| 19 | 4-phenyl-2-butanone | 46 (R) |
| 20 | 3-acetylthiophene | 84 (S) |
| 21 | 5-bromo-2-acetylthiophene | 78 (S) |
| 22 | 5-chloro-2-acetylthiophene | 78 (S) |
| 23 | 5-acetyl-2,4-dimethylthiazole | 71 (S) |
| 24 | 2-acetylbenzothiophene | 78 (S) |
| 25 | 3-acetylbenzothiophene | 78 (S) |
| 26 | 2-methoxyacetophenone | 79 (S) |
| 27 | 2-acetylfuran | 55 (S) |
| 28 | 3',5'-bis(trifluoromethyl)acetophenone | 74 (S) |
| 29 | methyl isopropyl ketone | 59 (R) |
| 30 | methyl isobutenyl ketone | 78 (unknown) |

Examples 31–36

The procedure was identical to Examples 7–12, respectively, with the exception that 250 microliter 0.1 M (25 micromoles) tetramethyl-2-t-butylguanidine in isopropanol was used instead of the sodium isopropoxide solution. In each example, the analysis showed the conversion of the ketone was 100% and the e.e of the chiral alcohol product was within one percentage point of that reported in Table 1 for the same ketone.

Examples 37–52

These Examples show the process of the invention for hydrogenation of acetophenone to nonracemic 1-phenethanol using a various amino-thioether ligands.

The procedure was identical to Example 2 with the exceptions that an equal molar amount of the amino-thioether ligand shown in Table 2 was substituted for the 2-(ethylthio)aniline and the reaction mixtures were stirred for the time shown in Table 2. The amino-thioether, the reaction time, the conversion of the acetophenone, the chirality of the 1-phenethanol, and its e.e. are given in Table 2.

TABLE 2

| Example | amino-thioether | Time (hours) | Conversion (%) | % e.e. (R/S) |
|---|---|---|---|---|
| 2 | 2-(ethylthio)aniline | 6 | 100 | 83 (S) |
| 37 | 2-(methylthio)aniline | 6 | 100 | 74 (S) |
| 38 | 2-(i-propylthio)aniline | 6 | 100 | 57 (S) |
| 39 | 2-(t-butylthio)aniline | 6 | 57 | 28 (S) |
| 40 | 2-(methylthio)-4-trifluoromethylaniline | 6 | 100 | 74 (S) |
| 41 | 2-(aminomethyl)thiophene | 14 | 100 | 24 (S) |
| 42 | 2-(methylthio)ethylamine | 6 | 100 | 11 (R) |
| 43 | 2-(ethylthio)ethylamine | 6 | 100 | 22 (R) |
| 44 | 2-(i-propylthio)ethylamine | 6 | 100 | 16 (R) |
| 45 | 2-(t-butylthio)ethylamine | 6 | 100 | 55 (R) |
| 46 | 2-(phenylthio)ethylamine | 14 | 100 | 14 (R) |
| 47 | 2-(benzylthio)ethylamine | 14 | 100 | 16 (R) |
| 48 | 3-(methylthio)-1-propylamine | 14 | 100 | 23 (S) |
| 49 | 3-(ethylthio)-1-propylamine | 14 | 100 | 3 (S) |
| 50 | 3-(i-propylthio)-1-propylamine | 14 | 100 | 15 (R) |
| 51 | 3-(t-butylthio)-1-propylamine | 14 | 100 | 4 (R) |
| 52 | 3-(phenylthio)-1-propylamine | 14 | 100 | 7 (R) |

These results demonstrate that a variety of amino-thioether ligands provide inventive catalyst systems having greater activity than corresponding catalysts system lacking an amino-thioether ligand (by comparison to the conversion in Comparative Example 1) and provide nonracemic 1-phenethanol (e.e.>0). The results further show that among the various amino-thioethers, the 2-(alkylthio)anilines generally give superior stereoselectivity in the hydrogenation of acetophenone when used in combination with the preferred nonracemic diphosphine ligands comprising a 2,2'-bis-(diorganophosphino)-1,1'-bis(cyclic) structure.

Examples 53–59

These Examples show the process of the invention for hydrogenation of acetophenone to nonracemic 1-phenethanol using a various based selected from alkylamidines, alkylguanidines, and aminophosphazenes.

The procedure was identical to Examples 1 and 2 with the exception that an equal molar amount of the base shown in Table 3 was substituted for the tetramethyl-2-t-butylguanidine (Example 1) or sodium isopropoxide (Example 2). In each example, the analysis showed the conversion of the ketone was 100% and (S)-1-phenethanol was formed in 83% e.e.

These results demonstrate that a variety of bases selected from alkylamidines, alkylguanidines, and aminophosphazenes provide inventive catalyst systems having activity at least comparable to that provided by sodium isopropoxide as the base.

TABLE 3

| Example | base |
|---|---|
| 53 | 1,5-diazabicyclo[4.3.0]non-5-ene |
| 54 | 1,5,7-triazabicyclo[4.4.0]dec-5-ene |
| 55 | 7-methyl-1,5,7-triazabicyclo[4.4.0]dec-5-ene |
| 56 | N,N,N',N',N",N"-hexamethyl-phosphorimidic triamide |
| 57 | N'"-t-butyl-N,N,N',N',N",N"-hexamethyl-phosphorimidic triamide |
| 58 | (t-butyl-imino)-tris(pyrrolidino)phosphorane |
| 59 | N'"-[N-ethyl-P,P-bis(dimethylamino)phosphinimyl]-N,N,N',N',N",N"-hexamethyl-phosphorimidic triamide |

Example 60

This Example show the process of the invention for hydrogenation of acetophenone to nonracemic 1-phenethanol using 2-butanol as the solvent.

The procedure was identical to Example 2 with the exceptions that 2-butanol was substituted for isopropanol in every occurrence except for the sodium isopropoxide solution and 125 microliter 0.2 M (25 micromoles) sodium isopropoxide in isopropanol was used instead of 63 microliter. The analysis showed 100% conversion of the acetophenone to give S-1-phenethanol with 82% e.e.

Examples 61–90

These Examples show the process of the invention for hydrogenation of acetophenone to nonracemic 1-phenethanol using various nonracemic diphosphine ligands in combinations with several amino-thioether ligands.

Stock solutions of [RuCl$_2$(diphosphine)(DMF)n] complexes were prepared identically to the preparation of the [RuCl$_2$(R,R,R,R-BICP)(DMF)n] as described in Preparation 1. The procedure for the hydrogenation reaction was identical to Example 2 with the exceptions that an equal molar amount the [RuCl$_2$(diphosphine)(DMF)n] having the diphosphine shown in Table 4 (abbreviations are given in the Detailed Description of the Invention) was substituted for [RuCl$_2$(R,R,R,R-BICP)(DMF)n], in some Examples an equal molar amount of the amino-thioether ligand shown in Table 4 was substituted for the 2-(ethylthio)aniline, in some Examples 125 microliter 0.2 M (25 micromoles, 20 equivalents to Ru) sodium isopropoxide in isopropanol was used instead of 63 microliter (12.5 micromoles, 10 equivalents to Ru), and the reaction mixtures were stirred for the time shown in Table 4. Table 4 gives the diphosphine, the amino-thioether, the equivalents of sodium isopropoxide to Ru, the reaction time, the conversion of the acetophenone, the absolute configuration of the 1-phenethanol, and its e.e.

These results demonstrate that a variety of nonracemic chiral diphosphine ligands provide the inventive catalyst systems for the hydrogenation of a ketone to a nonracemic chiral alcohol (e.e.>0). The results also show that different amino-thioethers give better stereoselectivities with different nonracemic chiral diphosphines and that for a given ketone reactant, a preferred combination of nonracemic chiral diphosphine and amino-thioether can be determined by routine experimentation. The results further show that among the various combinations, the combination of a preferred nonracemic diphosphine ligands comprising a 2,2'-bis-(diorgano-phosphino)-1,1'-bis(cyclic) structure (BICP) with a preferred amino-thioethers, 2-(ethylthio) aniline, gives substantially superior stereoselectivity in the hydrogenation of the prototypical ketone, acetophenone.

TABLE 4

| Ex. No. | diphosphine | amino-thioether | iPrONa (eq/Ru) | Time (hrs.) | Conv. (%) | % e.e. (R/S) |
|---|---|---|---|---|---|---|
| 2 | R,R,R,R-BICP | 2-(ethylthio)aniline | 10 | 6 | 100 | 83 (S) |
| 43 | R,R,R,R-BICP | 2-(ethylthio)ethylamine | 10 | 6 | 100 | 22 (R) |
| 45 | R,R,R,R-BICP | 2-(t-butylthio)ethylamine | 10 | 6 | 100 | 55 (R) |
| 61 | R,R-SKEWPHOS | 2-(ethylthio)aniline | 10 | 6 | 94 | 35 (S) |
| 62 | R,R-SKEWPHOS | 2-(ethylthio)ethylamine | 10 | 12 | 100 | 40 (S) |
| 63 | R,R-SKEWPHOS | 2-(t-butylthio)ethylamine | 20 | 12 | 100 | 48 (S) |
| 64 | S,S-CHIRAPHOS | 2-(ethylthio)aniline | 20 | 6 | 84 | 26 (R) |
| 65 | S,S-CHIRAPHOS | 2-(ethylthio)ethylamine | 20 | 6 | 100 | 38 (R) |
| 66 | S,S-CHIRAPHOS | 2-(t-butylthio)ethylamine | 20 | 6 | 100 | 27 (R) |
| 67 | R,R-DIOP | 2-(ethylthio)aniline | 10 | 6 | 100 | 29 (R) |
| 68 | R,R-DIOP | 2-(ethylthio)ethylamine | 20 | 12 | 100 | 3 (R) |
| 69 | R,R-DIOP | 2-(t-butylthio)ethylamine | 20 | 12 | 68 | 7 (S) |
| 70 | R,R-Me-PennPhos | 2-(ethylthio)aniline | 20 | 6 | 91 | 40 (S) |
| 71 | R,R-Me-PennPhos | 2-(ethylthio)ethylamine | 20 | 6 | 100 | 24 (R) |
| 72 | R,R-Me-PennPhos | 2-(t-butylthio)ethylamine | 20 | 6 | 100 | 26 (R) |
| 73 | R,R-Me-DuPHOS | 2-(ethylthio)aniline | 20 | 6 | 70 | 64 (S) |
| 74 | R,R-Me-DuPHOS | 2-(ethylthio)ethylamine | 20 | 6 | 86 | 33 (R) |
| 75 | R,R-Me-DuPHOS | 2-(t-butylthio)ethylamine | 20 | 6 | 39 | 12 (R) |
| 76 | R,R-Me-BPE | 2-(ethylthio)aniline | 20 | 12 | 16 | 19 (S) |
| 77 | R,R-Me-BPE | 2-(ethylthio)ethylamine | 20 | 12 | 62 | 15 (R) |
| 78 | R,R-Me-BPE | 2-(t-butylthio)ethylamine | 10 | 6 | 49 | 5 (R) |
| 79 | R-_BINAP | 2-(ethylthio)aniline | 10 | 6 | 38 | 14 (S) |
| 80 | R- = BINAP | 2-(ethylthio)ethylamine | 10 | 6 | 100 | 3 (R) |
| 81 | R- = BINAP | 2-(t-butylthio)ethylamine | 10 | 6 | 100 | 43 (S) |
| 82 | S- = MeOBIPHEP | 2-(ethylthio)aniline | 20 | 6 | 100 | 2 (R) |
| 83 | S- = MeOBIPHEP | 2-(ethylthio)ethylamine | 20 | 6 | 100 | 7 (R) |
| 84 | S- = MeOBIPHEP | 2-(t-butylthio)ethylamine | 20 | 6 | 100 | 27 (R) |
| 85 | R-C4-TunaPhos | 2-(ethylthio)aniline | 10 | 6 | 100 | 7 (S) |
| 86 | R-C4-TunaPhos | 2-(ethylthio)ethylamine | 10 | 6 | 100 | 2 (S) |
| 87 | R-C4-TunaPhos | 2-(t-butylthio)ethylamine | 20 | 6 | 100 | 11 (S) |
| 88 | S-f-BINAPHANE | 2-(ethylthio)aniline | 10 | 6 | 100 | 6 (S) |
| 89 | S-f-BINAPHANE | 2-(ethylthio)ethylamine | 20 | 12 | 31 | 8 (R) |
| 90 | S-f-BINAPHANE | 2-(t-butylthio)ethylamine | 20 | 12 | 14 | 17 (S) |

Examples 91–97

These Examples illustrate the inventive process for hydrogenation of 3',5'-bis-(trifluoromethyl)acetophenone to nonracemic 3',5'-bis(trifluoromethyl)-1-phenethanol using various nonracemic diphosphine ligands.

Solutions of [RuCl$_2$(diphosphine)(DMF)n] complexes, 500 micromolar in isopropanol, were prepared identically to the preparation of [RuCl$_2$(R,R,R,R-BICP)(DMF)n] described in Preparation 1. In the same manner as described in Example 1, solutions prepared, from 180 microliters (1.0 mmol) 3',5'-bis(trifluoromethyl)acetophenone, 10 mL 500 micromolar (5 micromoles) [RuCl$_2$(diphosphine)(DMF)n] in isopropanol, 0.20 mL 0.1 M (20 micromoles) 2-(ethylthio)aniline in isopropanol, and 0.10 mL 0.2 M (20 micromoles) sodium isopropoxide in isopropanol were stirred under 100 psi hydrogen for 6 hours at room temperature. In each example, the conversion of the 3',5'-bis (trifluoromethyl)acetophenone was complete. Table 5 gives the diphosphine, the chirality of the 3',5'-bis (trifluoromethyl)-1-phenethanol, and its e.e.

TABLE 5

| Example | diphosphine | % e.e. (R/S) |
|---------|-------------|--------------|
| 91 | R,R,R,R-BICP | 70 (AS) |
| 92 | R,R,R,R-3,5-Me$_8$BICP | 85 (S) |
| 93 | R,R-Me-PennPhos | 27 (AS) |
| 94 | R,R-iPr-PennPhos | 80 (AS) |
| 95 | R-MeOBIPHEP | 55 (R) |
| 96 | R,R-Me-DuPHOS | 10 (AS) |
| 97 | S-BiNAP | 59 (S) |

Examples 98–105

These Examples illustrate the inventive process for hydrogenation of 3',5'-bis-(trifluoromethyl)acetophenone to non-racemic 3',5'-bis(trifluoromethyl)-1-phenethanol in various solvents using tetramethyl-2-t-butylguanidine as the base.

Stock solutions of 556 micromolar [RuCl$_2$((R,R,R,R-BICP)(DMF)n] in various anhydrous, deaerated solvents were prepared analogous to the procedure in Preparation 1 by dissolving the solid residue comprising [RuCl$_2$(R,R,R,R-BICP)(DMF)n] in the desired solvent instead of isopropanol. In the same manner as described in Example 1, solutions prepared from 0.2843 g (1.11 mmol) 3',5'-bis (trifluoromethyl)acetophenone, 10 mL 556 micromolar (5.56 micromoles) [RuCl$_2$(R,R,R,R-BICP)(DMF)n] in the solvent, 0.22 mL 0.1 M (22 micromole) 2-(ethylthio)aniline in the solvent, and 0.20 mL 0.1 M (20 micromoles) tetramethyl-2-t-butylguanidine in the solvent were stirred under 100 psi hydrogen for 19 hours at room temperature. Table 6 gives the solvent, the conversion of the 3',5'-bis (trifluoro-methyl)acetophenone, and the e.e of the (S)-3',5'-bis(trifluoromethyl)-1-phenethanol product.

TABLE 6

| Example | solvent | Conv. (%) | % e.e. |
|---------|---------|-----------|--------|
| 98 | isopropanol | 100 | 72 |
| 99 | toluene | 100 | 77 |
| 100 | dibutyl ether | 100 | 75 |
| 101 | dichloromethane | 100 | 75 |
| 102 | chlorobenzene | 100 | 78 |
| 103 | ethylacetate | 37 | 74 |
| 104 | 1,2-dimethoxy ethane | 58 | 78 |
| 105 | methyl t-butyl ether | 24 | 70 |

These results show that that an organic base selected from alkylamidines, alkylguanidines, aminophosphazenes, and proazaphosphatranes allows the inventive process to be conducted using solvents other than alcohol solvents and in which basic salts such as sodium isopropoxide are not soluble.

Examples 106–110

These Examples illustrate the inventive process for hydrogenation of 3-(1-naphthalenyloxy)propiophenone to nonracemic 3-(1-naphthalenyloxy)-1-phenyl-1-propanol using preferred nonracemic diphosphine ligands comprising a 2,2'-bis(diorgano-phosphino)-1,1'-bis(cyclic) structure in combinations with several amino-thioether ligands.

In the same manner as described in Example 1, solutions prepared from 64 mg (250 mmol) 3-(1-naphthalenyloxy) propiophenone, 8.0 mL isopropanol, 2.0 mL 250 micromolar (0.5 micromoles) [RuCl$_2$(diphosphine)(DMF)n] in isopropanol, 0.10 mL 0.1 M (10 micromoles) amino-thioether in isopropanol, and 0.05 mL 0.2 M (10 micromole) sodium isopropoxide in isopropanol were stirred under 18 bar hydrogen for 17 hours at room temperature. In each example, the conversion of the 3-(1-naphthalenyloxy) propiophenone was complete. Table 7 gives the diphosphine, the amino-thioether, and the e.e. of the (R)-3-(1-naphthalenyloxy)-1-phenyl-1-propanol product.

TABLE 7

| Example | diphosphine | amino-thioether | % e.e. |
|---------|-------------|-----------------|--------|
| 106 | S,S,S,S-BICP | 2-(methylthio)aniline | 82 |
| 107 | S,S,S,S-BICP | 2-(ethylthio)aniline | 93 |
| 108 | S,S,S,S-BICP | 2-(i-propylthio)aniline | 66 |
| 109 | S,S,S,S-3,5-Me$_8$BICP | 2-(methylthio)aniline | 83 |
| 110 | S,S,S,S-3,5-Me$_8$BICP | 2-(ethylthio)aniline | 94 |

Examples 111 and 112

These Examples illustrate the process of the invention for the hydrogenation of more complex ketone reactant to a corresponding nonracemic chiral alcohol.

In a dry nitrogen-filled glovebox, each of two glass vials was charged with 1.0 mL 250 micromolar (0.25 micromoles) [RuCl$_2$((S,S,S,S-BICP)(DMF)n] in isopropanol, 9 mL isopropanol, 50 microliters 0.1 M (5.0 micromoles) 2-methylthioaniline in isopropanol. After stirring for about 2 minutes, 520 mg (1.25 mmol) (2S)-1-(4-benzyloxyphenyl)-2-(4-hydroxy-4-phenylpiperidin-1-yl)-1-propanone was added, followed by either 75 microliters 0.1 M (7.5 micromoles) tetramethyl-2-t-butylguanidine in isopropanol (Example 111) or 25 microliters 0.2 M (5.0 micromoles) sodium isopropoxide in isopropanol (Example 112). The glass vials containing the resulting suspensions were sealed in an autoclave, which was then removed from the glovebox. The gas phase in the autoclave was replaced by hydrogen at 18 bar. The gas-liquid mixtures were then stirred for 20 hours. Chiral HPLC analyses showed 99% conversion of the ketone to (1S,2S)-1-(4-benzoxyphenyl)-2-(4-hydroxy-4-phenylpiperidin-1-yl)-1-propanol, with >99% d.e., in each of the reactions.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A catalyst system useful for the hydrogenation of a ketone to a nonracemic chiral alcohol comprising ruthenium, a nonracemic chiral diphosphine ligand, an amino-thioether ligand, and a base.

2. The catalyst system of claim 1 wherein the nonracemic diphosphine ligand comprises a 2,2'-bis(diorganophosphino)-1,1'-bis(cyclic) structure.

3. The catalyst system of claim 2 wherein the nonracemic diphosphine ligand is selected from enantiomers of diphosphine ligands having the structural formula

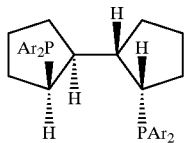

wherein Ar is an aryl group.

4. The catalyst system of claim 3 wherein Ar is selected from phenyl, monoalkylphenyl, dialkylphenyl, and trialkylphenyl.

5. The catalyst system of claim 1 wherein the aminothioether ligand is selected from 2-(alkylthio)ethylamines and 2-(alkylthio)anilines.

6. The catalyst system of claim 5 wherein the aminothioether is a 2-(alkylthio)aniline.

7. The catalyst system of claim 1 wherein the base is selected from basic inorganic and organic salts, alkylamidines, alkylguanidines, aminophosphazenes, and proazaphosphatranes.

8. The catalyst system of claim 7 wherein the base is selected from alkylamidines, alkylguanidines, aminophosphazenes, and proazaphosphatranes.

9. The catalyst system of claim 8 wherein the base is an alkylguanidine.

10. The catalyst system of claim 9 wherein the base is a pentaalkylguanidine.

* * * * *